(12) United States Patent
Tan et al.

(10) Patent No.: US 12,315,080 B2
(45) Date of Patent: May 27, 2025

(54) SYSTEM AND METHOD FOR DETECTING POSTURES OF A USER OF AN INFORMATION HANDLING SYSTEM (IHS)

(71) Applicant: Dell Products, L.P., Round Rock, TX (US)

(72) Inventors: Loo Shing Tan, Singapore (SG); Seng Khoon Teh, Singapore (SG)

(73) Assignee: Dell Products, L.P., Round Rock, TX (US)

( * ) Notice: Subject to any disclaimer, the term of this patent is extended or adjusted under 35 U.S.C. 154(b) by 477 days.

(21) Appl. No.: 17/664,473

(22) Filed: May 23, 2022

(65) Prior Publication Data

US 2023/0377264 A1 Nov. 23, 2023

(51) Int. Cl.
G06K 9/00 (2022.01)
G06T 17/20 (2006.01)
G06V 10/762 (2022.01)
G06V 10/766 (2022.01)
G06V 40/16 (2022.01)

(52) U.S. Cl.
CPC ............ *G06T 17/20* (2013.01); *G06V 10/762* (2022.01); *G06V 10/766* (2022.01); *G06V 40/161* (2022.01); *G06V 40/171* (2022.01); *G06V 40/172* (2022.01)

(58) Field of Classification Search
CPC ...... G06F 1/1616; G06F 1/1681; G06F 3/017; G06F 3/013; G06F 1/1677; G06F 1/1643; G06F 1/1618; G06F 1/1652; G06F 3/011; G06F 3/038; G06F 3/0393; G06F 3/016; G06F 3/012; G06F 1/1694; G06F 1/1669; G06F 1/203; G06F 1/206; G06F 3/04883; G06F 1/1641; G06F 1/1656; G06F 3/0416; G06F 1/1637; G06T 19/006; G06T 7/70; G06T 2207/10048; G06T 2207/10028; G06T 19/20; G06T 7/579; G06T 2207/10024; G06T 2207/30196; G06T 7/285; G06T 11/001; G06T 11/60
See application file for complete search history.

(56) References Cited

U.S. PATENT DOCUMENTS

| | | | | |
|---|---|---|---|---|
| 2012/0214594 A1* | 8/2012 | Kirovski | ............... | A63F 13/814 463/36 |
| 2015/0158178 A1* | 6/2015 | Burmeister | ........... | G06T 1/0014 382/203 |
| 2019/0139297 A1* | 5/2019 | Chen | ....................... | G06T 19/20 |
| 2020/0380259 A1* | 12/2020 | Cahill | ..................... | G06T 13/40 |
| 2021/0390748 A1* | 12/2021 | Liao | ....................... | G06V 10/82 |

* cited by examiner

*Primary Examiner* — Alex Kok S Liew
(74) *Attorney, Agent, or Firm* — Fogarty LLP

(57) ABSTRACT

Methods and systems are provided for determining a posture of a user of an Information Handling System (IHS). One or more cameras of the IHS are utilized to generate a two-dimensional image of the user as they operate the IHS. Landmarks that correspond to physical features of the user are identified through processing of the two-dimensional image generated using the cameras. The system then identifies, from a database comprising a plurality of differing wireframes, a subset of the wireframes that optimally match the physical feature landmarks of the user, each of the wireframes associated with an ergonomic level, and performs a regression analysis technique on the ergonomic level of each of the subset of wireframes to determine a posture score of the user.

20 Claims, 5 Drawing Sheets

SYSTEM AND METHOD FOR DETECTING POSTURES OF A USER OF AN INFORMATION HANDLING SYSTEM (IHS)

BACKGROUND

As the value and use of information continues to increase, individuals and businesses seek additional ways to process and store information. One option is an Information Handling System (IHS). An IHS generally processes, compiles, stores, and/or communicates information or data for business, personal, or other purposes. Because technology and information handling needs and requirements may vary between different applications, IHSs may also vary regarding what information is handled, how the information is handled, how much information is processed, stored, or communicated, and how quickly and efficiently the information may be processed, stored, or communicated. The variations in IHSs allow for IHSs to be general or configured for a specific user or specific use such as financial transaction processing, airline reservations, enterprise data storage, global communications, etc. In addition, IHSs may include a variety of hardware and software components that may be configured to process, store, and communicate information and may include one or more computer systems, data storage systems, and networking systems.

IHSs that are utilized for personal use, such personal computers, laptops, tablets, smartphones, etc., are increasingly likely to be regularly utilized for long intervals of time. Uninterrupted use of IHSs without breaks has been demonstrated to be potentially harmful, both physically and psychologically, to the user. For instance, users may experience physical side effects from regular and continued use of an IHS while physically positioned in non-ergonomic postures, such as while slouching in a chair.

SUMMARY

Embodiments of the present disclosure are provided for determining a posture of a user of an Information Handling System (IHS). One or more cameras of the IHS are utilized to generate a two-dimensional image of the user as they operate the IHS. Landmarks that correspond to physical features of the user are identified through processing of the two-dimensional image generated using the cameras. The system then identifies, from a database comprising a plurality of differing wireframes, a subset of the wireframes that optimally match the physical feature landmarks of the user, each of the wireframes associated with an ergonomic level, and performs a regression analysis technique on the ergonomic level of each of the subset of wireframes to determine a posture score of the user.

According to another embodiment, a posture estimation method includes the steps of utilizing one or more cameras of an Information Handling System (IHS) to generate a two-dimensional (2D) image of a user of the HIS, and identifying a plurality of physical feature landmarks of the user in the two-dimensional image. The method further includes the steps of identifying, from a database comprising a plurality of differing wireframes, a subset of the wireframes that optimally match the physical feature landmarks of the user, each of the wireframes associated with an ergonomic level, and performing a regression analysis technique on the ergonomic level of each of the subset of wireframes to determine a posture score of the user.

According to yet another embodiment, a computer program product including a computer readable storage medium having program instructions embodied therewith in which the program instructions are executable by a processor to utilize the one or more cameras of the IHS to generate a two-dimensional (2D) image of a user of the HIS, identify a plurality of physical feature landmarks of the user in the two-dimensional image, and identify, from a database comprising a plurality of differing wireframes, a subset of the wireframes that optimally match the physical feature landmarks of the user, each of the wireframes associated with an ergonomic level. The program instructions are further executable to perform a regression analysis technique on the ergonomic level of each of the subset of wireframes to determine a posture score of the user.

BRIEF DESCRIPTION OF THE DRAWINGS

The present invention(s) is/are illustrated by way of example and is/are not limited by the accompanying figures, in which like references indicate similar elements. Elements in the figures are illustrated for simplicity and clarity, and have not necessarily been drawn to scale.

DETAILED DESCRIPTION

The present disclosure is described with reference to the attached figures. The figures are not drawn to scale, and they are provided merely to illustrate the disclosure. Several aspects of the disclosure are described below with reference to example applications for illustration. It should be understood that numerous specific details, relationships, and methods are set forth to provide an understanding of the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

Wellness devices generally refer to those devices that aid users in selecting lifestyles or activities that enhances their overall health. Examples of such wellness devices may include, for example, fitness watches, blood pressure/heart rate monitors, and blood sugar testing devices to name a few. Due to the advent of portable computing devices, such as laptop computers, and smartphones, wellness applications have been developed that leverage the capabilities of those devices. One example of a wellness application may include a SIGNALS application provided by DELL TECHNOLO- GIES. One goal of the SIGNALS application is to periodically measure a user's sitting posture for providing retrospective insight for the user to be aware of the estimated amount of time spent sitting in an upright position as compared to a non-upright position. This information is intended to work with other gamification capabilities in SIGNALS application to nudge the user towards a better sitting posture in order to minimize unhealthy consequences, such as musculoskeletal disorder (MSD).

To measure a user's posture, a camera of the user's computing device (IHS) may be used along with a suitable algorithm to estimate a posture level of the user. However, most cameras configured on personal computing device are front-facing cameras. That is, the front-facing camera only captures a frontal plane image of the user who is typically sitting or standing in front of the computing device. This poses two main issues: i) practically, there is a need to observe from a sagittal plane of a person to determine whether a person is sitting in an upright position as compared to a non-upright position as a frontal plane image can only provide partial information pertaining to a sagittal plane, and ii) as the person is sitting or standing in front of the computing device, at most a partial frontal field of the user is available to determine whether the user is sitting in an upright position, thereby complicating the aforementioned issue.

Figure 1:
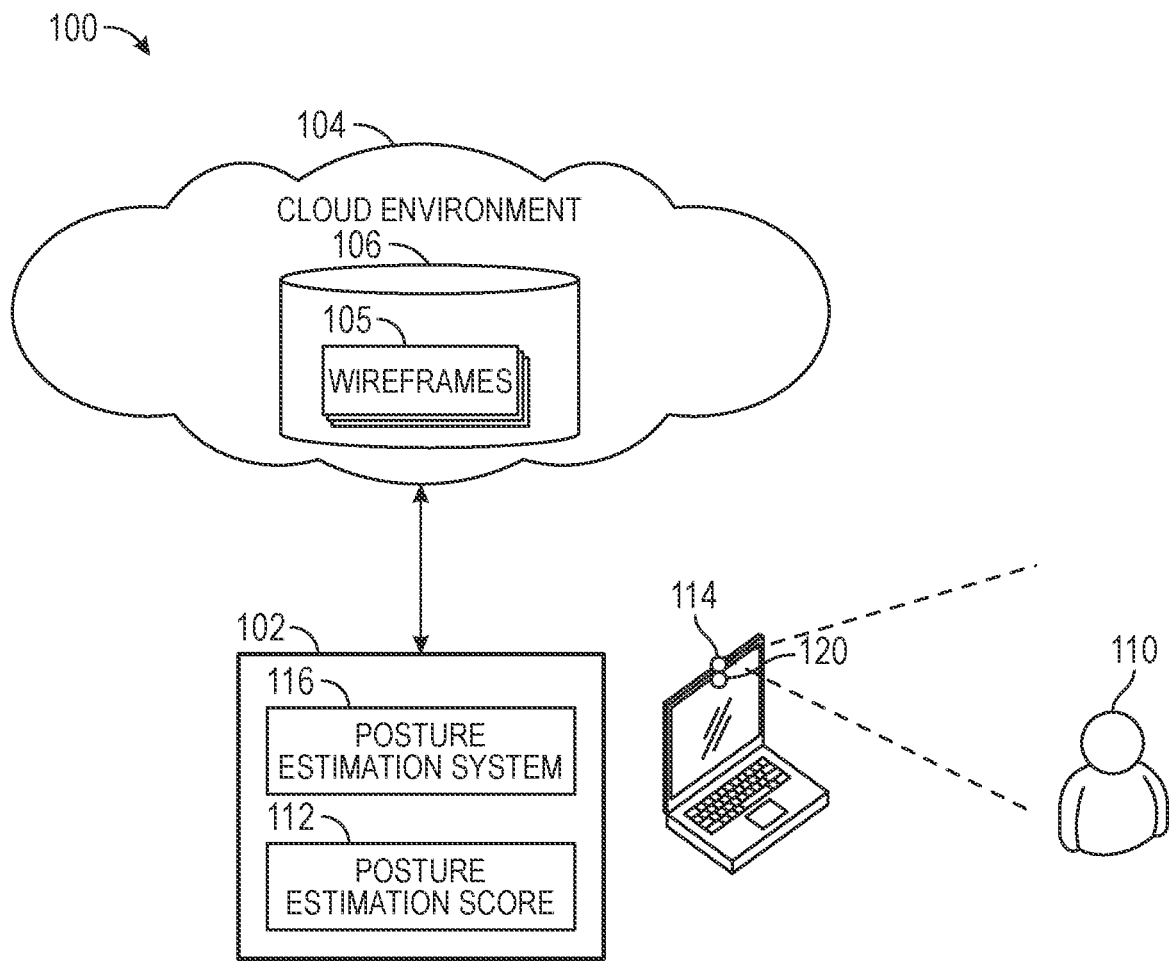
FIG. 1 illustrates an example 3D posture estimating system according to one embodiment of the present disclosure that may provide a solution to the aforementioned problems with front-facing cameras.

FIG. 1 illustrates an example 3D posture estimating system 100 according to one embodiment of the present disclosure that may provide a solution to the aforementioned problems with front-facing cameras. The system 100 includes an IHS 102 in communication with a cloud environment 104 (e.g., IHS support portal) that stores a database 106 of differing wireframes 108. The IHS 102 includes an executable posture estimation engine 116 that receives an image of a user 110 from a camera 114 of the IHS 102, and in conjunction with the IHS support 104, processes the image by accessing the wireframes 108 stored in the cloud environment portal 104 to estimate a posture score 112. While the present embodiment describes the IHS 102 as accessing the wireframes 108 from an external cloud environment 104, it should be appreciated that in other embodiments, the wireframes 108 may be stored in the IHS 102 so that the system 100 may access the wireframes 108 from an internal memory of the IHS 102, thus negating the need for the cloud environment 104 in some embodiments.

The user will typically operate the IHS while facing an integrated display of the IHS, or in some cases an external display that is coupled to the IHS. The physical characteristics in which the user holds their body while operating the IHS may be referred to as the user's posture. Postures that are considered ergonomic are those in which the user is aligned and positioned relative to the IHS such that the user's body is not unnecessarily strained. As described, operating an IHS for prolonged periods of time while positioned in non-ergonomic postures may result in the user experience a variety of physical symptoms.

The camera capabilities of the IHS are used to capture a two-dimensional image with the camera settings of the IHS configured to focus the camera on the user that is positioned at their expected location while operating the IHS, such as facing the display screen of the IHS from approximately an arms-length distance from the display screen as illustrated in FIG. 1. In this manner, the camera capabilities of the IHS may be used to capture an image of the user as they face the display of the IHS as they operate the IHS. In some cases, the captured image may then be processed in order to isolate the user from the rest of the image, and in particular to isolate the user from the background behind the user and from any surfaces in front of the user, such as from a desk or table.

The system 100 may use the estimated posture score 112 in any suitable manner for aiding the user in enhancing their posture. For example, the posture score 112 may be periodically checked against a specified threshold value such that when it is exceeded, the system 100 may generate an alert message to the user 110. As another example, the posture score 112 may be used as an input value to another machine learning (ML) process for identifying certain epochs or periods of time when the user's posture becomes less than desirable. That is, the ML process may identify a particular application (e.g., gaming application) that when executed by the user, causes that user's overall posture to suffer. As yet another example, the system 100 may generate a histogram that may be provided to the user 110 at periodic levels (e.g., each week, each month, etc.) to show how the user's posture has been maintained during the preceding time period.

To estimate whether a person is sitting in an upright or non-upright position from the use of only a partial frontal plane view provided by the camera 114, which on many portable IHSs, such as laptop computers and smart phones, is a front-facing camera, the system 100 leverages a 2D human pose estimation technique to record certain key physical feature landmarks (e.g., joint coordinate data, the user's eyes, shoulders, mouth, nose, chin, and top of the user's head, etc.) of the user 110, accessing the database 106 that stores multiple wireframes 108 of a person seated in an upright or non-upright position, and comparing the physical feature landmarks against the wireframes 108 for estimating the probability of sitting in an upright position of the user 110. That is, the system 100 utilizes the camera 114 of the IHS 102 to generate a two-dimensional image of the user 110, identifies multiple physical feature landmarks of the user based on the two-dimensional image generated by the camera 114, and identifies, a subset of the wireframes that optimally match the physical feature landmarks of the user, each of the wireframes associated with an ergonomic level from a database comprising a plurality of differing wireframes 108. As will be described in detail herein below, the system 100 may then use the subset of wireframes to perform a regression analysis technique on the ergonomic level of each of the subset of wireframes to determine a posture score 112 of the user.

For purposes of this disclosure, an IHS may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, an IHS may be a personal computer (e.g., desktop or laptop), tablet computer, mobile device (e.g., Personal Digital Assistant (PDA) or smart phone), server (e.g., blade server or rack server), a network storage device, or any other suitable device and may vary in size, shape, performance, functionality, and price. An IHS may include Random Access Memory (RAM), one or more processing resources, such as a Central Processing Unit (CPU) or hardware or software control logic, Read-Only Memory (ROM), and/or other types of nonvolatile memory.

Additional components of an IHS may include one or more disk drives, one or more network ports for communicating with external devices as well as various I/O devices, such as a keyboard, a mouse, touchscreen, and/or a video display. An IHS may also include one or more buses operable to transmit communications between the various hardware components. An example of an IHS is described in more detail below. FIG. 1 shows an example of an IHS configured to implement the systems and methods described herein according to certain embodiments. It should be appreciated that although certain IHS embodiments described herein may be discussed in the context of a personal computing device, other embodiments may be utilized.

Figure 2:
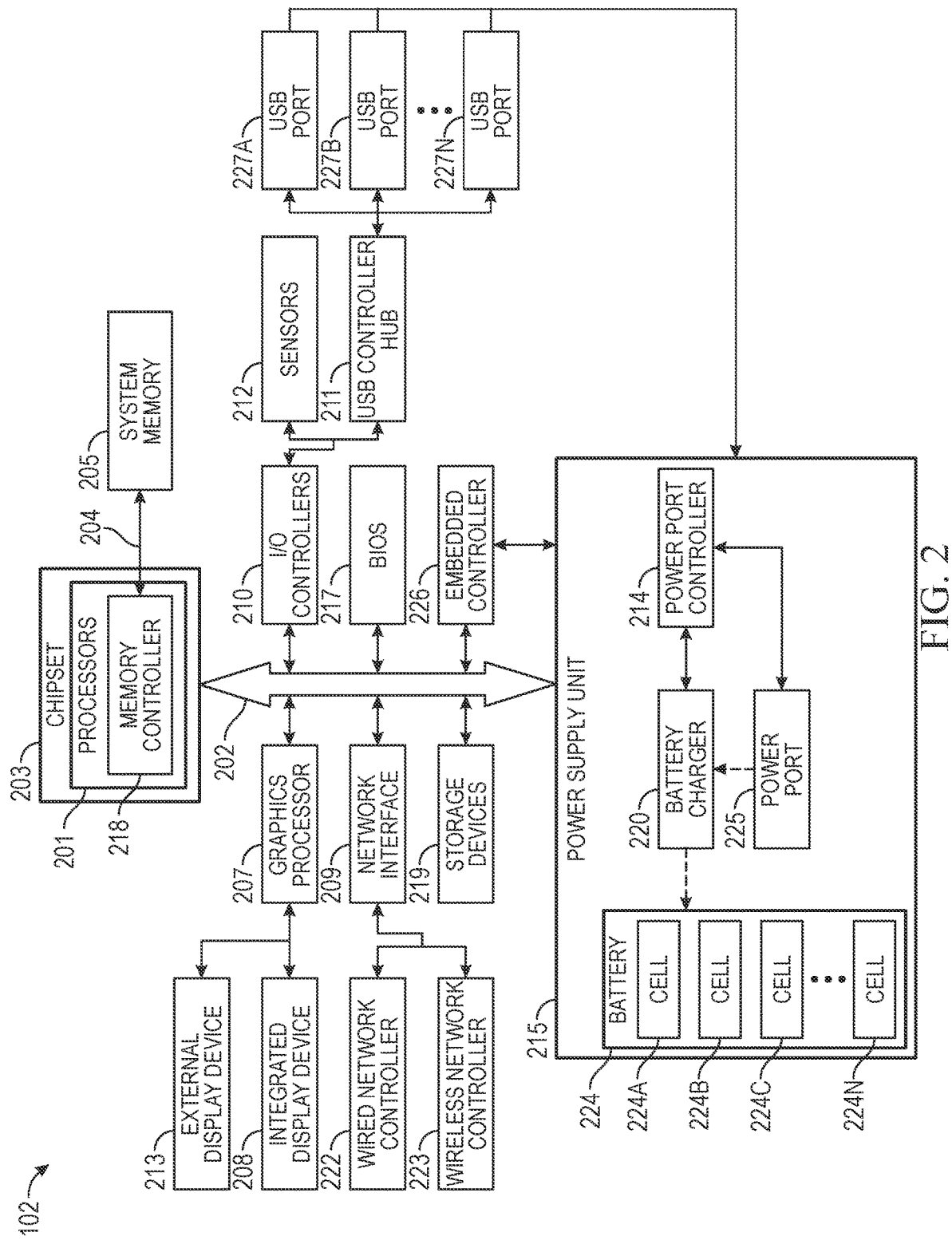
FIG. 2 is a block diagram depicting certain components of an IHS operable according to various embodiments for detecting physical postures of a user of the IHS.

FIG. 2 is a block diagram depicting certain components of an IHS 102 operable according to various embodiments for detecting physical postures of a user of the IHS. As described in additional detail below, IHS 102 may include capabilities for identifying and evaluating the posture in which the user of IHS 102 is physically positioned relative to the IHS, where such determinations may be made based on data collected from various I/O capabilities supported by the IHS 102. In addition, embodiments may also utilize data collected by the IHS 102 to estimate levels of risk posed by identified postures of the user. In various embodiments, IHS 102 may include an embedded controller 226 that includes logic that executes program instructions, in conjunction with operations by components of power supply unit 215 and the operating system of IHS 102, to perform the operations disclosed herein for collecting data for use in detecting physical postures of a user of the IHS 102. While a single IHS 102 is illustrated in FIG. 2, IHS 102 may be a component of an enterprise system that may include any number of additional IHSs that may also be configured in the same or similar manner to IHS 102.

IHS 102 includes one or more processors 201, such as a Central Processing Unit (CPU), that execute code retrieved from a system memory 205. Although IHS 102 is illustrated with a single processor 201, other embodiments may include two or more processors, that may each be configured identically, or to provide specialized processing functions. Processor 201 may include any processor capable of executing program instructions, such as an Intel Pentium™ series processor or any general-purpose or embedded processors implementing any of a variety of Instruction Set Architectures (ISAs), such as the x86, POWERPC®, ARM®, SPARC®, or MIPS® ISAs, or any other suitable ISA.

In the embodiment of FIG. 2, the processor 201 includes an integrated memory controller 218 that may be implemented directly within the circuitry of the processor 201, or the memory controller 218 may be a separate integrated circuit that is located on the same die as the processor 201. The memory controller 218 may be configured to manage the transfer of data to and from the system memory 205 of the IHS 102 via a high-speed memory interface 204. The system memory 205 that is coupled to processor 201 provides the processor 201 with a high-speed memory that may be used in the execution of computer program instructions by the processor 201. Accordingly, system memory 205 may include memory components, such as such as static RAM (SRAM), dynamic RAM (DRAM), NAND Flash memory, suitable for supporting high-speed memory operations by the processor 201. In certain embodiments, system memory 205 may combine both persistent, non-volatile memory and volatile memory. In certain embodiments, the system memory 205 may be comprised of multiple removable memory modules.

IHS 102 utilizes a chipset 203 that may include one or more integrated circuits that are connected to processor 201. In the embodiment of FIG. 2, processor 201 is depicted as a component of chipset 203. In other embodiments, all of chipset 203, or portions of chipset 203 may be implemented directly within the integrated circuitry of the processor 201. Chipset 203 provides the processor(s) 201 with access to a variety of resources accessible via bus 202. In IHS 102, bus 202 is illustrated as a single element. Various embodiments may utilize any number of buses to provide the illustrated pathways served by bus 202.

As illustrated, a variety of resources may be coupled to the processor(s) 201 of the IHS 102 through the chipset 203. For instance, chipset 203 may be coupled to a network interface 209 that may support different types of network connectivity. In certain embodiments, IHS 102 may include one or more Network Interface Controllers (NICs), each of which may implement the hardware required for communicating via a specific networking technology, such as Wi-Fi, BLUETOOTH, Ethernet, and mobile cellular networks (e.g., CDMA, TDMA, LTE). As illustrated, network interface 209 may support network connections by wired network controllers 222 and wireless network controller 223. Each network controller 222, 223 may be coupled via various buses to the chipset 203 of IHS 102 in supporting different types of network connectivity, such as the network connectivity utilized by applications of the operating system of IHS 102.

Chipset 203 may also provide access to one or more display device(s) 208, 213 via graphics processor 207. In certain embodiments, graphics processor 207 may be comprised within a video or graphics card or within an embedded controller installed within IHS 102. In certain embodiments, graphics processor 207 may be integrated within processor 201, such as a component of a system-on-chip. Graphics processor 207 may generate display information and provide the generated information to one or more display device(s) 208, 213 coupled to the IHS 102. The one or more display devices 208, 213 coupled to IHS 102 may utilize LCD, LED, OLED, or other display technologies. Each display device 208, 213 may be capable of receiving touch inputs such as via a touch controller that may be an embedded component of the display device 208, 213 or graphics processor 207, or may be a separate component of IHS 102 accessed via bus 202. As illustrated, IHS 102 may support an integrated display device 208, such as a display integrated into a laptop, tablet, 2-in-1 convertible device, or mobile device. In some embodiments, IHS 102 may be a hybrid laptop computer that includes dual integrated displays incorporated in both of the laptop panels. IHS 102 may also support use of one or more external displays 213, such as external monitors that may be coupled to IHS 102 via various types of couplings.

In certain embodiments, chipset 203 may utilize one or more I/O controllers 210 that may each support hardware components such as user I/O devices and sensors 212. For instance, I/O controller 210 may provide access to one or more user I/O devices such as a keyboard, mouse, touchpad, touchscreen, microphone, speakers, camera and other input and output devices that may be coupled to IHS 102. Each of the supported user I/O devices may interface with the I/O controller 210 through wired or wireless connections. In some embodiments, the I/O devices that may be accessible by IHS 102 may include one or more cameras, that may be an integrated component of the IHS, or that may be an external device coupled to the IHS through a wired or wireless coupling. As described in additional detail below, embodiments may utilize one or more cameras of the IHS in identifying and evaluating the posture in which the user of IHS 102 is physically positioned relative to the IHS. In particular, two-dimensional images captured using the camera capabilities of the IHS may be used to identify and locate landmark features of a user, which may be used in determining the posture in which the user is currently positioned, relative to the IHS.

In certain embodiments, sensors 212 that may be accessed via I/O controllers 210 may provide access to data describing environmental and operating conditions of IHS 102. For instance, sensors 212 may include geo-location sensors capable for providing a geographic location for IHS 102, such as a GPS sensor or other location sensors configured to determine the location of IHS 102 based on triangulation and network information. Various additional sensors, such as optical, infrared and sonar sensors, that may provide support for xR (virtual, augmented, mixed reality) sessions hosted by the IHS 102. Such sensors 212 may capabilities for detecting when a user is detected within a certain proximity to IHS 102. For instance, sensors 212 may detect when a user is in close proximity to the IHS 102 and, in some cases, whether the user is facing the display(s) 208, 213.

As illustrated, I/O controllers 210 may include a USB controller 211 that, in some embodiments, may also implement functions of a USB hub. In some embodiments, USB controller 211 may be a dedicated microcontroller that is coupled to the motherboard of IHS 102. In other embodiments, USB controller 211 may be implemented as a function of another component, such as a component of a SoC (System on Chip) of IHS 102, embedded controller 226, processors 201 or of an operating system of IHS 102. USB controller 211 supports communications between IHS 102 and one or more USB devices coupled to IHS 102, whether the USB devices are coupled to IHS 102 via wired or wireless connections. In some embodiments, a USB controller 211 may operate one or more USB drivers that detect the coupling of USB devices and/or power inputs to USB ports 227a-n. USB controller 211 may include drivers that implement functions for supporting communications between IHS 102 and coupled USB devices, where the USB drivers may support communications according to various USB protocols (e.g., USB 2.0, USB 3.0). In providing functions of a hub, USB controller 211 may support concurrent couplings by multiple USB devices via one or more USB ports 227a-n supported by IHS 102.

Chipset 203 also provides processor 201 with access to one or more storage devices 219. In various embodiments, storage device 219 may be integral to the IHS 102, or may be external to the IHS 102. In certain embodiments, storage device 219 may be accessed via a storage controller that may be an integrated component of the storage device. Storage device 219 may be implemented using any memory technology allowing IHS 102 to store and retrieve data. For instance, storage device 219 may be a magnetic hard disk storage drive or a solid-state storage drive. In certain embodiments, storage device 219 may be a system of storage devices, such as a cloud drive accessible via network interface 209.

As illustrated, IHS 102 also includes a BIOS (Basic Input/Output System) 217 that may be stored in a non-volatile memory accessible by chipset 203 via bus 202. In some embodiments, BIOS 217 may be implemented using a dedicated microcontroller coupled to the motherboard of IHS 102. In some embodiments, BIOS 217 may be implemented as operations of embedded controller 226. Upon powering or restarting IHS 102, processor(s) 201 may utilize BIOS 217 instructions to initialize and test hardware components coupled to the IHS 102. The BIOS 217 instructions may also load an operating system for use by the IHS 102. The BIOS 217 provides an abstraction layer that allows the operating system to interface with the hardware components of the IHS 102. The Unified Extensible Firmware Interface (UEFI) was designed as a successor to BIOS. As a result, many modern IHSs utilize UEFI in addition to or instead of a BIOS. As used herein, BIOS is intended to also encompass UEFI.

Some IHS 102 embodiments may utilize an embedded controller 226 that may be a motherboard component of IHS 102 and may include one or more logic units. In certain embodiments, embedded controller 226 may operate from a separate power plane from the main processors 201, and thus from the operating system functions of IHS 102. In some embodiments, firmware instructions utilized by embedded controller 226 may be used to operate a secure execution environment that may include operations for providing various core functions of IHS 102, such as power management and management of certain operating modes of IHS 102.

Embedded controller 226 may also implement operations for interfacing with a power supply unit 215 in managing power for IHS 102. In certain instances, the operations of embedded controller may determine the power status of IHS 102, such as whether IHS 102 is operating strictly from battery power, whether any charging inputs are being received by power supply unit 215, and/or the appropriate mode for charging the one or more battery cells 224a-n using the available charging inputs. Embedded controller 226 may support routing and use of power inputs received via a USB port 227a-n and/or via a power port 225 supported by the power supply unit 215. In addition, operations of embedded controller 226 may interoperate with power supply unit 215 in order to provide battery status information, such as the charge level of the cells 224a-n of battery 224. In some embodiments, power status information collected by embedded controller 226 may be utilized in determining whether to operate user activity monitoring procedures, where the monitoring of user activity is used to determine when the user is actively operating the IHS 102 and when the user has taken a break from operating the IHS.

In some embodiments, embedded controller 226 may also interface with power supply unit 215 in monitoring the battery state of battery 224, such as the relative state of charge of battery 224, where this charge level of the battery 224 may be specified as a percentage of the full charge capacity of the battery 224. In some instance, when operating from power stored in battery system 224, embedded controller 226 may detect when the voltage of the battery system 224 drops below a low-voltage threshold. When the charge level of battery 224 drops below such a low-voltage threshold, embedded controller 226 may transition the IHS to an off-power state in implementing a battery protection mode that preserves a minimal power level in battery 224.

Embedded controller 226 may also implement operations for detecting certain changes to the physical configuration of IHS 102 and managing the modes corresponding to different physical configurations of IHS 102. For instance, where IHS 102 is a laptop computer or a convertible laptop computer, embedded controller 226 may receive inputs from a lid position sensor that may detect whether the two sides of the laptop have been latched together, such that the IHS is in a closed position. In response to lid position sensor detecting latching of the lid of IHS 102, embedded controller 226 may initiate operations for shutting down IHS 102 or placing IHS 102 in a low-power mode. In this manner, IHS 102 may support the use of various power modes. In some embodiments, the power modes of IHS 102 may be implemented through operations of the embedded controller 226 and power supply unit 215.

As described, IHS 102 may also include a power supply unit 215 that receives power inputs used for charging batteries 224 from which the IHS 102 operates. IHS 102 may include a power port 225 to which an AC adapter may be coupled to provide IHS 102 with a supply of DC power. The DC power input received at power port 225 may be utilized by a battery charger 220 for recharging one or more internal batteries 224 of IHS 102. As illustrated, batteries 224 utilized by IHS 102 may include one or more cells 224a-n that may connected in series or in parallel. Power supply unit 215 may support various modes for charging the cells 224a-n of battery 224 based on the power supply available to IHS 102 and based on the charge levels of the battery system 224. In certain embodiments, power supply unit 215 of IHS 102 may include a power port controller 214 that is operable for configuring operations by power port 225.

In various embodiments, an IHS 102 does not include each of the components shown in FIG. 2. In various embodiments, an IHS 102 may include various additional components in addition to those that are shown in FIG. 2. Furthermore, some components that are represented as separate components in FIG. 2 may in certain embodiments instead be integrated with other components. For example, in certain embodiments, all or a portion of the functionality provided by the illustrated components may instead be provided by components integrated into the one or more processor(s) 201 as a systems-on-a-chip.

Figure 3:
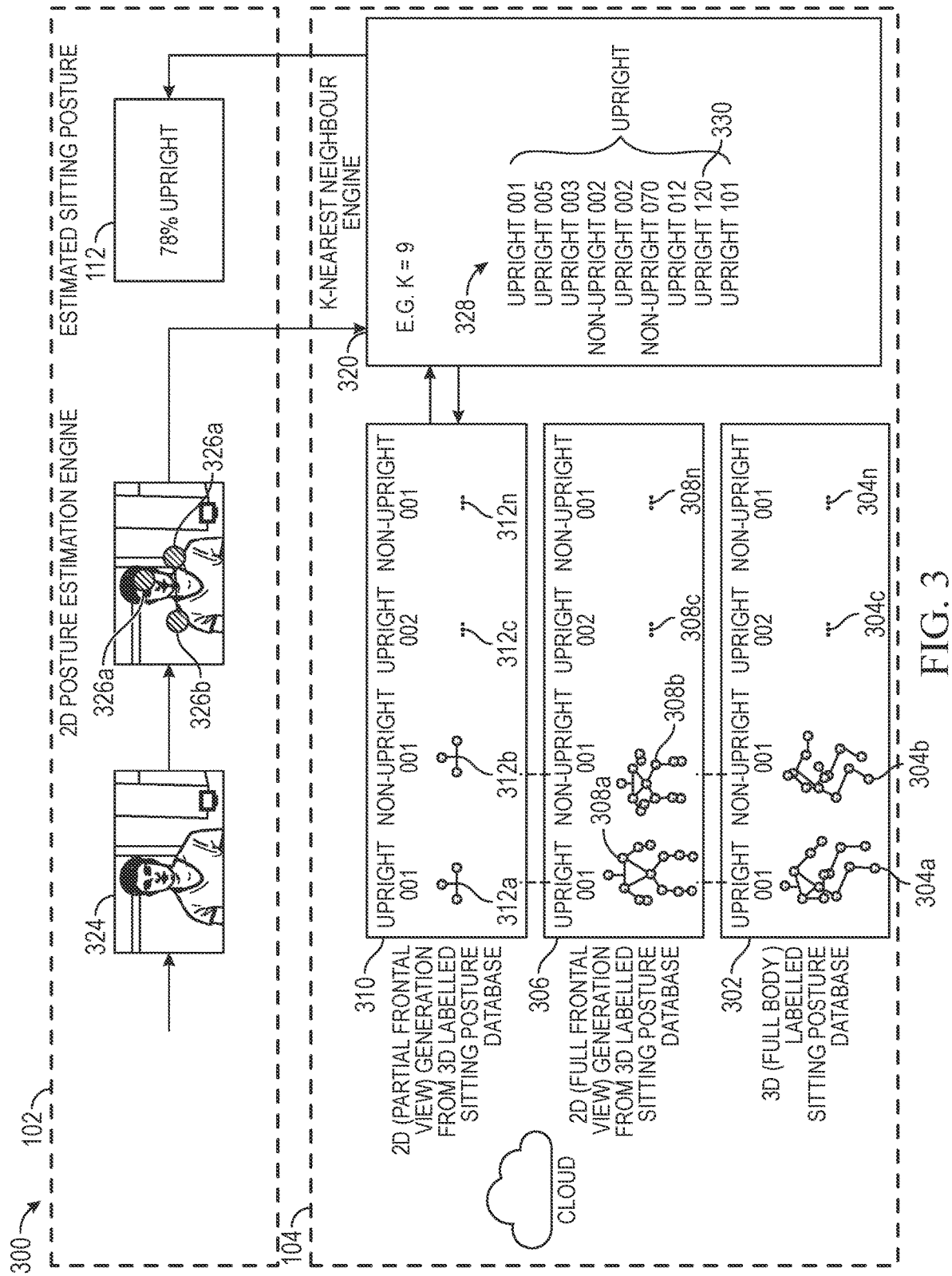
FIG. 3 illustrates several example components of the 3D posture estimating system that may be used to obtain a posture score that will be provided to the user to indicate the probability of sitting in an upright position according to one embodiment of the present disclosure.

FIG. 3 illustrates several example components of the 3D posture estimating system 100 that may be used to obtain a posture score that will be provided to the user to indicate the probability of sitting in an upright position according to one embodiment of the present disclosure. As shown, the cloud environment 104 of the system 100 includes a database 302 that stores multiple different 3D full body wireframes 304a-n (collectively 304), a database 306 that stores multiple 2D full body wireframes 308a-n (collectively 308), and a database 310 that stores multiple 2D partial frontal wireframes 312a-n (collectively 312). The cloud environment 104 also includes a k-nearest neighbor engine 320 that determines a posture score 112 as will be described in detail herein below.

When the user 110 is positioned in front of the IHS 102, the posture estimation engine 116 uses the camera 114 to record a frontal plane image 324 of the user 110 sitting or standing in front of the IHS 102, and deploy the 2D human pose estimation model to derive key physical feature landmarks 326a-b (collectively 326). In the set of landmarks 326, landmarks 326a may correspond to the location of the user's eyes and landmarks 326b may correspond to the location of the ends of each of the user's shoulders.

To determine the probability of the user sitting in an upright or in a non-upright position, the posture estimation engine 116 may send the physical feature landmarks to the cloud environment 104, which uses a regression analysis technique (e.g., k-nearest neighbor engine) for obtaining a posture score 112 that will be returned to the PC for the user to comprehend the probability of sitting in an upright position. Although the present embodiment uses a k-nearest neighbor engine 320 to obtain the posture score 112, it should be appreciated that any suitable regression analysis technique may be used without departing from the spirit and scope of the present disclosure.

The 3D full body wireframes 304 generally represent models of human structure with varying levels of posture ranging from non-ergonomic (e.g., bad posture) to ergonomic (e.g., good posture). The 3D full body wireframes 304 may be obtained from actual human images or created using 3D computer aided drawing technology. Additionally, the database 302 can grow with new 3D full body wireframes 304 over time to cater to more variation of a human posture sitting or standing in front of the IHS 102.

The 2D full body wireframes 308 are created from the 3D full body wireframes 304 by mapping their physical feature landmarks in a rotated plane so that the 2D full body wireframes 308 represent what each corresponding 3D full body wireframe 308 would look like if viewed from the front. The 2D partial body wireframes 312 are created from the 2D full body wireframes 308 to remove certain features (e.g., physical feature landmarks) below the torso are removed. Such a feature may be particularly useful due to the fact that in many cases, only the physical feature landmarks above the torso can be seen by the camera 114 of the IHS 102. Furthermore, removing these features would reduce the amount of memory required to store all of the 2D partial body wireframes 312. The k-nearest neighbor engine 320 will seek to learn from the (2D partial frontal view) database 310, which in turn is derived from the (2D full frontal view) database 306, and in turn, is derived from the (3D full body) posture database 302.

To provide a particular example, when the k-nearest neighbor engine 320 receives the physical feature landmarks 326 from the IHS 102, it may identify those 2D partial body wireframes 312 that optimally match the physical feature landmarks 326, which in the example is shown with 9 2D partial body wireframes 328. An ergonomic level 330 is associated with each 2D partial body wireframe 328 indicating its posture level. The k-nearest neighbor engine 320 averages the ergonomic levels 330 to obtain an overall posture score, which in this particular example is 78 percent (%) upright. The posture score 112 is then sent to the IHS 102 to be used as described above with reference to the description of FIG. 1.

Figure 4:
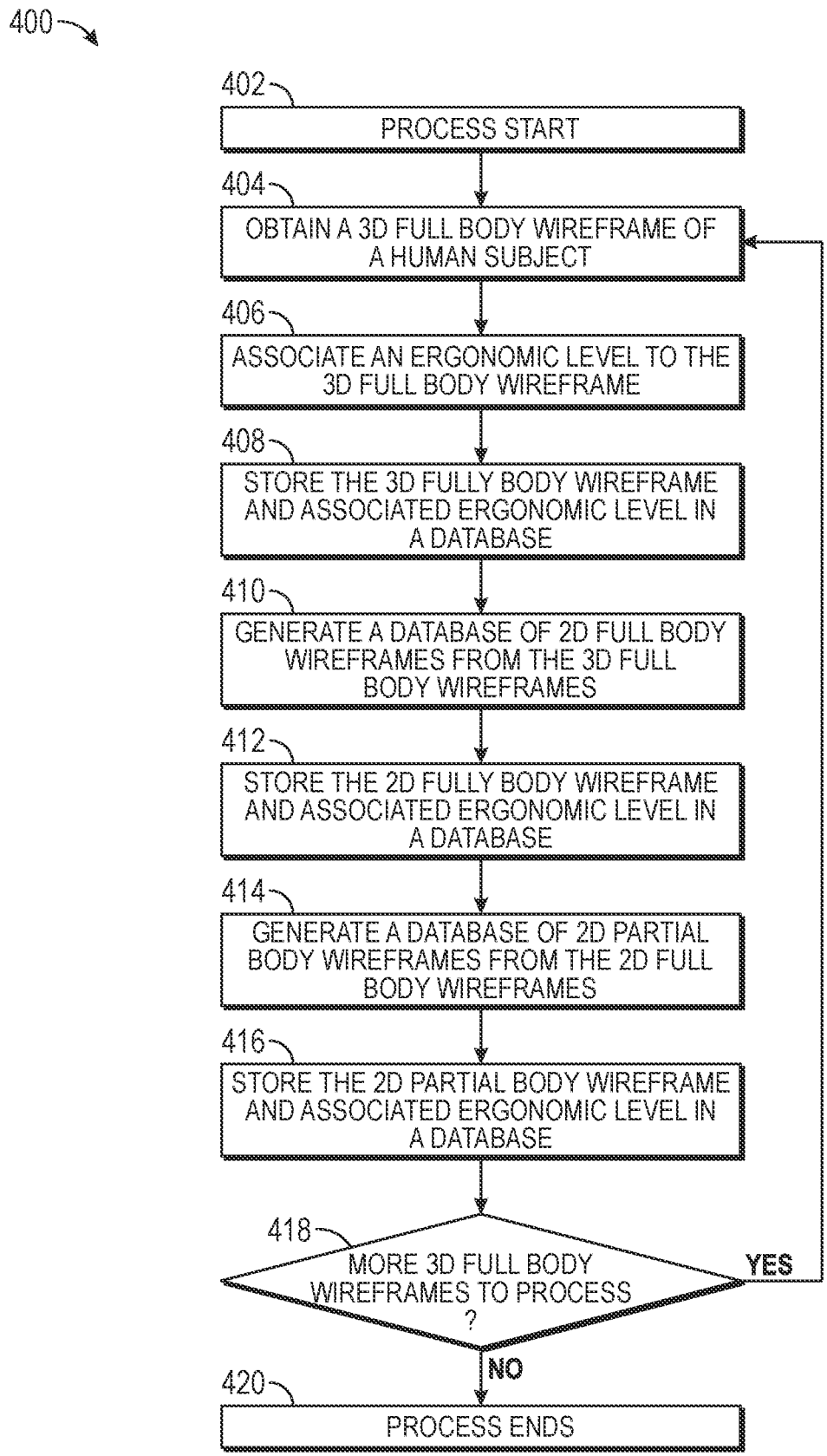
FIG. 4 illustrates an example wireframe database creation method that may be used to generate the database of 2D partial body wireframes according to one embodiment of the present disclosure.

FIG. 4 illustrates an example wireframe database creation method 400 that may be used to generate the database 310 of 2D partial body wireframes 312 according to one embodiment of the present disclosure. The method 400 may be performed by any set of instructions that are stored in a memory and executed by a processor. In one embodiment, the method 400 may be performed by the posture estimation engine 116. Additionally or alternatively, certain steps of the method 400 may be performed by the posture estimation engine 116, while other steps are performed by the cloud environment 104. The method 400 can be performed at any time, such as initially to create a new database of 2D partial body wireframes 312, or at an ensuing period of time to add new 2D partial body wireframes 312 to an existing database.

At step 402, the method 400 starts. At step 404, the method 400 obtains a 3D full body wireframe of a human subject. In other embodiments, the 3D full body wireframe may be obtained using 3D computer aided technology. In another embodiment, the 3D full body wireframe may be generated from a standing human subject or a sitting human subject. Thereafter at step 406, the method 400 associates an ergonomic level to the 3D full body wireframe. For example, the method 400 may receive user input from a user who has assessed a posture level of the human subject. The method 400 then stores the 3D fully body wireframe and associated ergonomic level in a database at step 408.

At step 410, the method 400 generates a database of 2D full body wireframes from the 3D full body wireframes using known 3D to 2D conversion techniques, and then stores the 2D fully body wireframe and its associated ergonomic level in a database at step 412. Thereafter at step 414, the method 400 generate another database of 2D partial body wireframes from the 2D full body wireframes followed by storing the 2D partial body wireframe and its associated ergonomic level in another database at step 416.

At step 418, the method 400 determines whether more 3D full body wireframes needs to be processed. For example, the method 400 may be partially finished with processing a batch of 3D images for a new database, or it may be adding a new 3D image to an existing database. In either case, if more 3D full body wireframes need to be processed, processing continues at step 404; otherwise, processing continues at step 420 in which the process ends.

Figure 5:
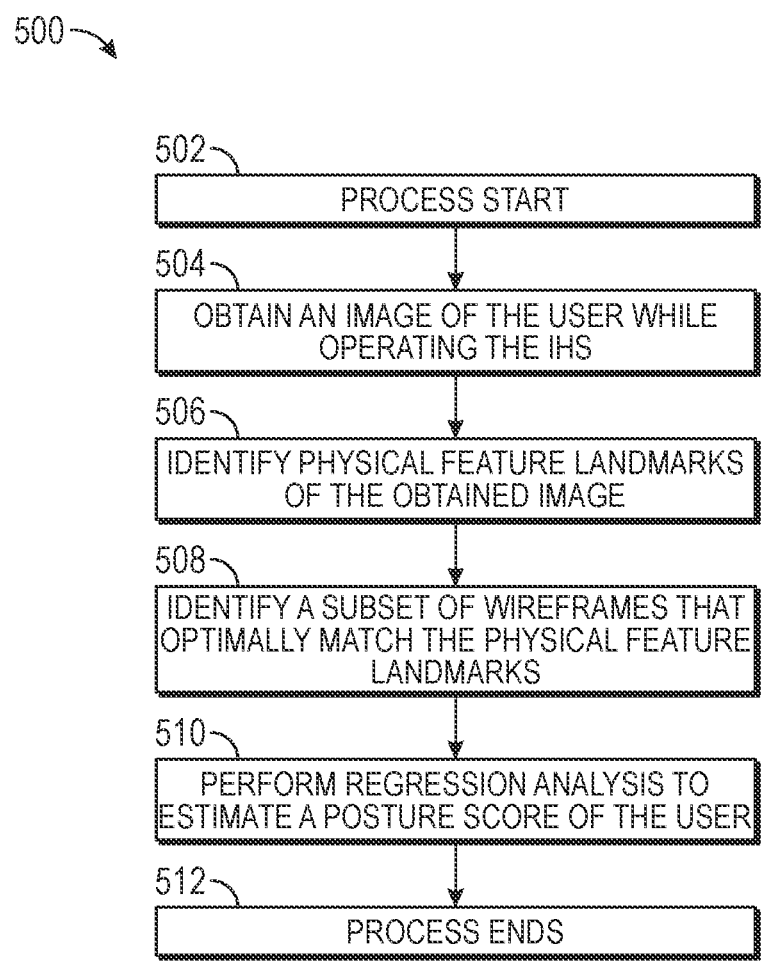
FIG. 5 illustrates an example 3D posture estimating method 500 that may be used to estimate a posture of a user of an IHS according to one embodiment of the present disclosure.

FIG. 5 illustrates an example 3D posture estimating method 500 that may be used to estimate a posture of a user of an IHS 102 according to one embodiment of the present disclosure. The method 500 may be performed by any set of instructions that are stored in a memory and executed by a processor, such as by those included in the cloud environment 104 and/or by the IHS 102. Additionally or alternatively, certain steps of the method 500 may be performed by the IHS 102, while other steps are performed by the cloud environment 104. The method 500 can be performed at ongoing intervals to continually assess the posture of the user. In one embodiment, the rate at which the method 500 is performed may be adjusted based on certain factors, such as when the posture level of the user deteriorates or improves, during certain periods of the day (e.g., morning, lunch time, afternoon, evening, night, etc.), and/or in response to detecting a lack of movement and/or activity by the user for over a certain duration of time. Embodiments of the present disclosure may generate a risk score based on the detected posture of the user, where the risk score quantifies the risk of physical side effects for particular non-ergonomic postures. In such embodiments, embodiments may initiate posture detection procedures more regularly as the risk scores for the user's posture increase. As such, embodiments may detect postures more frequently for users with poor ergonomics.

At step 502, the method 500 starts. At step 504, the method 500 obtains an image of the user while operating the IHS. For example, the image of the user may be obtained from a front-facing camera of the IHS 102. The camera capabilities of the IHS are used to capture a two-dimensional image with the camera settings of the IHS configured to focus the camera on the user that is positioned at their expected location while operating the IHS, such as facing the display screen of the IHS from approximately an arms-length distance from the display screen as illustrated in FIG. 1. In this manner, the camera capabilities of the IHS may be used to capture an image of the user as they face the display of the IHS as they operate the IHS. In some cases, the captured image may then be processed in order to isolate the user from the rest of the image, and in particular to isolate the user from the background behind the user and from any surfaces in front of the user, such as from a desk or table.

At step 506, the method 500 identifies multiple physical feature landmarks of the obtained image. In some embodiments, the method 500 may rely on biometric image processing capabilities that are available to the IHS in order to identify such physical feature landmarks 326 in the captured image of the user. In such embodiments, the landmark features 326 of the user may be identified using a library of biometric prints of the user, where the biometric prints may specify the relative locations of the landmark features of the user, when the user is at a certain distance and orientation relative to the IHS. In some cases, the method 500 may generate a map of the identified landmarks features of the user, such as illustrated map of landmarks 326 of FIG. 3, where the map may include the locations of each of the physical landmarks on a coordinate plane, which may correspond to a vertical plane of the user.

Thereafter at step 508, the method 500 identifies a subset of wireframes that optimally match the physical feature landmarks. The method 500 may identify the subset of wireframes using a cloud environment 104, or using instructions executed locally in the IHS 102. In one embodiment, the method 500 may use a supervised learning technique, such as a k-nearest neighbor engine to identify the subset of wireframes. At step 510, the method 500 performs a regression analysis to estimate a posture score of the user. In one embodiment, the method 500 may calculate a cumulative average of the ergonomic levels of each of the subset of wireframes to estimate the posture of the user. Once the posture score has been obtained, it may be used for various purposes, such as to notify the user when his or her posture has deteriorated below a certain specified threshold level, as an input to another ML process to infer other properties of the user, or to generate a histogram for formulating assessments of lifestyle changes of the user over time. Nevertheless, at step 512 the method 500 ends.

Although FIGS. 4 and 5 describe example methods 400 and 500 that may be performed for estimating a posture level of a user, the features of the methods 400 and 500 may be embodied in other specific forms without deviating from the spirit and scope of the present disclosure. For example, the methods 400 and 500 may perform additional, fewer, or different operations than those described in the present examples. As another example, the steps of the aforedescribed methods 400 and 500 may be performed in a sequence other than what is described above. As yet another example, some, most, or all steps of the methods 400 and/or 500 may be performed by an IHS other than the IHS 102 or the cloud environment 104.

It should be understood that various operations described herein may be implemented in software executed by processing circuitry, hardware, or a combination thereof. The order in which each operation of a given method is performed may be changed, and various operations may be added, reordered, combined, omitted, modified, etc. It is intended that the invention(s) described herein embrace all such modifications and changes and, accordingly, the above description should be regarded in an illustrative rather than a restrictive sense.

The terms "tangible" and "non-transitory," as used herein, are intended to describe a computer-readable storage medium (or "memory") excluding propagating electromagnetic signals; but are not intended to otherwise limit the type of physical computer-readable storage device that is encompassed by the phrase computer-readable medium or memory. For instance, the terms "non-transitory computer readable medium" or "tangible memory" are intended to encompass types of storage devices that do not necessarily store information permanently, including, for example, RAM. Program instructions and data stored on a tangible computer-accessible storage medium in non-transitory form may afterwards be transmitted by transmission media or signals such as electrical, electromagnetic, or digital signals, which may be conveyed via a communication medium such as a network and/or a wireless link.

Although the invention(s) is/are described herein with reference to specific embodiments, various modifications and changes can be made without departing from the scope of the present invention(s), as set forth in the claims below. Accordingly, the specification and figures are to be regarded in an illustrative rather than a restrictive sense, and all such modifications are intended to be included within the scope of the present invention(s). Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

The invention claimed is:

1. An Information Handling System (IHS) comprising:
one or more processors;
one or more cameras;
a memory device coupled to the one or more processors, the memory device storing computer-readable instructions that, upon execution by the one or more processors, cause the IHS to:
utilize the one or more cameras of the IHS to generate a two-dimensional (2D) image of a user of the IHS;
identify a plurality of physical feature landmarks of the user in the two-dimensional image;
identify, from a database comprising a plurality of differing wireframes, a subset of the wireframes that optimally match the physical feature landmarks of the user, each of the wireframes associated with an ergonomic level; and
perform a regression analysis technique on the ergonomic level of each of the subset of wireframes to determine a posture score of the user, wherein the posture score comprises a slouching level of the user while the user is using the IHS.

2. The IHS of claim 1, wherein the instructions, upon execution, cause the IHS to:
derive a plurality of 2D full frontal view wireframes from a plurality of differing three-dimensional (3D) full body wireframes; and
derive a plurality of 2D partial frontal view wireframes from the plurality of 2D full frontal view wireframes, wherein the plurality of 2D partial frontal view wireframes comprise the plurality of differing wireframes.

3. The IHS of claim 2, wherein the 3D full body wireframes are generated from at least one of actual human images or 3D computer aided drawings.

4. The IHS of claim 1, wherein the wireframes comprise at least one of standing wireframes and sitting wireframes.

5. The IHS of claim 1, wherein the instructions, upon execution, further cause the IHS to utilize a front facing camera of the IHS to generate the 2D image of the user, wherein the IHS comprises at least one of a workstation or a laptop computer.

6. The IHS of claim 1, wherein the instructions, upon execution, further cause the IHS to identify the subset of wireframes using a supervised learning technique.

7. The IHS of claim 6, wherein the supervised learning technique comprises a k-nearest neighbor technique.

8. The IHS of claim 1, wherein the instructions, upon execution, cause the IHS to transmit the plurality of physical feature landmarks to a cloud environment, wherein the acts of identifying the subset of wireframes and performing the regression analysis are performed by the cloud environment, and wherein the database of differing wireframes are stored in the cloud environment.

9. The IHS of claim 1, wherein the instructions, upon execution, cause the IHS to identify the subset of wireframes and perform the regression analysis technique using instructions stored in the memory of the IHS.

10. The IHS of claim 1, wherein the physical feature landmarks comprise locations corresponding to at least one of the user's eyes, shoulders, mouth, nose, chin, and top of the user's head.

11. A posture estimation method comprising:
utilizing one or more cameras of an Information Handling System (IHS) to generate a two-dimensional (2D) image of a user of the IHS;
identifying a plurality of physical feature landmarks of the user in the two-dimensional image;
identifying, from a database comprising a plurality of differing wireframes, a subset of the wireframes that optimally match the physical feature landmarks of the user, each of the wireframes associated with an ergonomic level; and
performing a regression analysis technique on the ergonomic level of each of the subset of wireframes to determine a posture score of the user, wherein the posture score comprises a slouching level of the user while the user is using the IHS.

12. The posture estimation method of claim 11, further comprising:
deriving a plurality of 2D full frontal view wireframes from a plurality of differing three-dimensional (3D) full body wireframes; and
deriving a plurality of 2D partial frontal view wireframes from the plurality of 2D full frontal view wireframes, wherein the plurality of 2D partial frontal view wireframes comprise the plurality of differing wireframes.

13. The posture estimation method of claim 12, further comprising generating the 3D full body wireframes are generated from at least one of actual human images or 3D computer aided drawings.

14. The posture estimation method of claim 11, further comprising utilizing a front facing camera of the IHS to generate the 2D image of the user, wherein the IHS comprises at least one of a workstation or a laptop computer.

15. The posture estimation method of claim 11, further comprising identifying the subset of wireframes using a supervised learning technique comprising a k-nearest neighbor engine.

16. The posture estimation method of claim 11, further comprising transmitting the plurality of physical feature landmarks to a cloud environment, wherein the acts of identifying the subset of wireframes and performing the regression analysis are performed by the cloud environment, and wherein the database of differing wireframes are stored in the cloud environment.

17. A computer program product comprising a computer readable storage medium having program instructions embodied therewith, the program instructions executable by a processor to cause the processor to perform the following:
- utilize the one or more cameras of the IHS to generate a two-dimensional (2D) image of a user of the IHS;
- identify a plurality of physical feature landmarks of the user in the two-dimensional image;
- identify, from a database comprising a plurality of differing wireframes, a subset of the wireframes that optimally match the physical feature landmarks of the user, each of the wireframes associated with an ergonomic level; and
- perform a regression analysis technique on the ergonomic level of each of the subset of wireframes to determine a posture score of the user, wherein the posture score comprises a slouching level of the user while the user is using the IHS.

18. The computer program product of claim 17, wherein the instructions, upon execution, cause the processor to:
- derive a plurality of 2D full frontal view wireframes from a plurality of differing three-dimensional (3D) full body wireframes; and
- derive a plurality of 2D partial frontal view wireframes from the plurality of 2D full frontal view wireframes, wherein the plurality of 2D partial frontal view wireframes comprise the plurality of differing wireframes.

19. The computer program product of claim 17, wherein the instructions, upon execution, further cause the processor to identify the subset of wireframes using a supervised learning technique comprising a k-nearest neighbor technique.

20. The computer program product of claim 17, wherein the instructions, upon execution, cause the processor to transmit the plurality of physical feature landmarks to a cloud environment, wherein the acts of identifying the subset of wireframes and performing the regression analysis are performed by the cloud environment, and wherein the database of differing wireframes are stored in the cloud environment.

* * * * *